United States Patent [19]

Kuekenhoehner et al.

[11] Patent Number: 5,350,863
[45] Date of Patent: Sep. 27, 1994

[54] PREPARATION OF 3-(2'-OXYETHYL)DIHYDRO-2(3H)FURANONES

[75] Inventors: Thomas Kuekenhoehner, Boehl-Iggelheim; Norbert Goetz, Worms; Rolf Fischer, Heidelberg; Werner Schnurr, Herxheim; Dirk Borchers, Birkenheide, all of Fed. Rep. of Germany

[73] Assignee: BASF Aktiengesellschaft, Ludwigshafen, Fed. Rep. of Germany

[21] Appl. No.: 120,439

[22] Filed: Sep. 14, 1993

[30] Foreign Application Priority Data

Sep. 18, 1992 [DE] Fed. Rep. of Germany ....... 4231297

[51] Int. Cl.$^5$ ............................................. C07D 307/20
[52] U.S. Cl. .................................................. 549/323
[58] Field of Search ....................................... 549/323

[56] References Cited

U.S. PATENT DOCUMENTS 4,831,166 5/1989 Eckhardt et al. ............. 549/323

FOREIGN PATENT DOCUMENTS 546573 of 0000 Canada .
194144 9/1986 European Pat. Off. .
899558 1/1982 U.S.S.R. ...................... 549/423

OTHER PUBLICATIONS

Dokl. Akad. Nauk SSSR 27, (1940) 956–959.
Dokl. Akad, Nauk SSSR 29, (1940) 579 to 581.
Liebige Ann., 116, (1860) 252.
Angew. Chem. 84, 1972 1173.
Lipkin et al., Khim–Farm. Zh., 23(1), p. 70 (1989).
Chem. Abst. vol. 35, No. 5, Mar. 10, 1941, Abst. No. 1382.5.
Chem. Abst. vol. 35, No. 11, Jun. 10, 1941, Abst. No. 3627.9.

*Primary Examiner*—Bernard Dentz
*Attorney, Agent, or Firm*—Keil & Weinkauf

[57] ABSTRACT

A process for preparing 3-(2'-oxyethyl)dihydro-2(3H)furanones of the general formula I

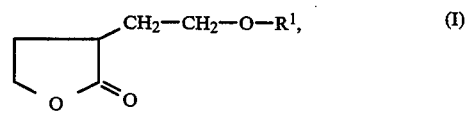

where $R^1$ is hydrogen or acetyl, by reacting ethylene oxide with acetoacetic acid esters of the general formula II

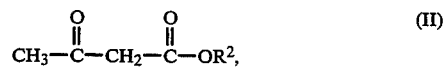

where $R^2$ is $C_1$–$C_4$-alkyl, which comprises carrying out the reaction in alcoholic solutions in the presence of alkali metal alkoxides at from 20° to 100° C. and from 1 to 20 bar, is described.

8 Claims, No Drawings

PREPARATION OF 3-(2'-OXYETHYL)DIHYDRO-2(3H)FURANONES

The invention relates to an improved process for preparing 3-(2'-oxyethyl)dihydro-2(3H) furanones by reacting ethylene oxide with acetoacetic acid esters with alkali metal alkoxide catalysis.

The preparation of 3-(2'-acetoxyethyl) dihydro-2(3H) furanone by acylating 3-(2'-hydroxyethyl) dihydro-2(3H)furanone with acetic anhydride is known from Dokl. Akad. Nauk SSSR 27, (1940) 956 to 959.

The preparation of 3-(2'-hydroxyethyl)dihydro-2(3H) furanone by reacting ethyl acetoacetate with ethylene oxide in the presence of catalytic amounts of a weak base such as e.g. piperidine at room temperature over 20 days is known from Dokl. Akad. Nauk SSSR 29, (1940) 579 to 581. Long reaction times of this type are industrially unsuitable. Ethylene oxide furthermore reacts with these catalysts to give quaternary ammonium salts which interfere in the work-up.

In addition, U.S. Pat. No. 4,831,166 discloses the use of other weak bases and the catalytic action of neutral salts, such as alkali metal halides, ammonium halides, phosphonium halides, alkali metal phosphates or alkali metal carbonates, in the reaction of alkyl acetoacetates with ethylene oxide to give 3-(2'-hydroxyethyl)dihydro-2(3H)furanone. Depending on the type and amount of solvent used, a mixture of 3-(2'-hydroxyethyl)dihydro-2(3H) furanone and 3-(2'-acetoxyethyl)dihydro-2(3H) furanone is obtained in this reaction. For industrial use, however, of the catalysts described are of only limited suitability, since many of them such as e.g. sodium chloride, alkali metal phosphates or alkali metal carbonates are not soluble in the solvents used, so that the reaction has to be carried out in a heterogeneous mixture; on the other hand, when using halide salts small amounts of 2-haloethanols are formed from the halide ions and ethylene oxide (Liebigs Ann., 116, (1860) 252; Angew. Chem. 84, (1972) 1173)), which have very toxic properties and have to be separated off carefully, with great cost, from the product since in many subsequent reactions such as e.g. during catalytic ester hydrogenation with hydrogen they result in catalyst poisoning even in ppm amounts as a result of their halogen content.

Reactions of acetoacetic acid esters with ethylene oxide using catalytic or stoichiometric amounts of strong bases, such as e.g. sodium methoxide or sodium hydroxide solution at from ($-10$) to $+40°$ C. for long reaction times are known, e.g. from Helv. Chim. Acta 35, (1952) 2401, EP-A-348 549, U.S. Pat. No. 2,433,827 and CA-A-546 573, the product described being 3-acetyldihydro-2(3H) furanone, i.e. the addition product of one equivalent of ethylene oxide to the acetoacetic ester.

In addition, the decomposition of 3-acetyldihydro-2(3H)furanone by alcoholic alkoxide solutions is known from Khim.-Farm. Zh., 23 (1), (1989) 70.

It is an object of the present invention to remedy the disadvantages previously mentioned.

We have found that this object is achieved by a novel and improved process for preparing 3-(2'-oxyethyl)-dihydro-2(3H) furanones of the general formula (I)

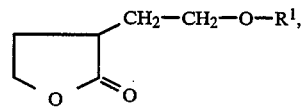

where R is hydrogen or acetyl

by reacting ethylene oxide with acetoacetic acid esters of the general formula II

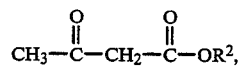

where $R^2$ is $C_1$–$C_4$-alkyl, which comprises carrying out the reaction in alcoholic solutions in the presence of alkali metal alkoxides at from 20 to 100° C. and from 1 to 20 bar.

The process according to the invention can be carried out as follows:

For preparing the 3-(2'-oxyethyl)dihydro-2(3H)furanones I, the acetoacetic acid ester II is as a rule initially introduced in alcoholic solution in the presence of an alkali metal alkoxide at from 20 to 100° C., preferably 40 to 80° C., particularly preferably 50 to 70° C. and from 1 to 20 bar, preferably 1.5 to 10 bar, particularly preferably 2 to 5 bar, and the ethylene oxide, which is liquid as a rule, is metered into this mixture with intensive stirring.

It may be advantageous to carry out the reaction using a temperature gradient. For example, during the metering in of the ethylene oxide the reaction can be carried out at low temperatures from 40 to 60° C. and then, to complete the reaction, at a higher temperature of from 60 to 80° C.

The reaction is customarily carried out in sealed stirred reactors, since some of the reaction components, in particular ethylene oxide, are sometimes gaseous at the reaction temperatures and only partly dissolve in the reaction mixture. A superatmospheric pressure which approximately corresponds to the partial vapor pressures of reaction components is therefore as a rule established in the reactor. The pressure is additionally dependent on the reaction temperature.

The molar ratio of ethylene oxide to the acetoacetic acid ester II is as a rule 3:1–1:1, preferably 2.2:1–1.5:1, particularly preferably 2:1.

Suitable acetoacetic acid esters II are in principle esters of any desired alcohols such as $C_1$–$C_{20}$-alcohols. As a rule, esters of the $C_1$–$C_4$-alcohols are used, preferably methyl acetoacetate and ethyl acetoacetate, particularly preferably methyl acetoacetate.

Suitable alkali metal alkoxides are lithium, sodium, potassium, rubidium and cesium alkoxides, preferably lithium, sodium and potassium alkoxides of any desired -alcohols such as $C_1$–$C_{20}$-alcohols. As a rule, alkali metal alkoxides of $C_1$–$C_4$-alcohols such as sodium methoxide, sodium ethoxide, potassium methoxide, potassium ethoxide and potassium tert-butoxide are used, preferably alkali metal alkoxides of $C_1$- and $C_2$-alcohols such as sodium methoxide, sodium ethoxide, potassium methoxide and potassium ethoxide, particularly preferably sodium methoxide.

The molar ratio of alkali metal alkoxide to the acetoacetic acid ester II is as a rule 0.001:1–1:1, preferably 0.01:1–0.5:1, particularly preferably 0.02:1–0.2:1.

The alkali metal alkoxides can be employed in the reaction as solids. For process engineering reasons, however, it is advantageous to work with solutions of the alkali metal alkoxides. In principle, all solvents can be used which are stable to the alkoxides used and under the reaction conditions. An alcoholic solution of the alkali metal alkoxides proves particularly advantageous, since this solution can be simply prepared, e.g. by dissolving the particular alkali metal in the alcohol concerned. A solution of sodium methoxide in methanol is particularly preferred.

Suitable solvents are all customary alcohols such as $C_1$–$C_{20}$-alcohols, preferably $C_1$–$C_4$-alcohols such as methanol, ethanol, propanol, isopropanol, butanol, sec-butanol, isobutanol and tert-butanol, particularly preferably methanol and ethanol; to achieve good reactions results it is unnecessary for the solvent, alcohol component of the ester group in the acetoacetic ester II and alcohol component of the alkali metal alkoxide catalyst to be identical.

The amount of solvent can be selected from within a wide range, but it is expediently from 25 to 500 ml, preferably 50 to 200 ml, of per mole of acetic ester II.

Transesterification reactions customarily take place under the alkaline reaction conditions. A mixture of 3-(2'-acetoxyethyl)dihydro-2(3H)furanone and 3-(2'-hydroxyethyl)dihydro-2(3H)furanone, which is formed as a secondary product of 3-(2'-acetoxyethyl)dihydro-2(3H)furanone by methanolysis under the alkaline reaction conditions, is therefore as a rule obtained. The ratio of 3-(2'-hydroxyethyl)dihydro-2(3H) furanone and 3-(2'-acetoxyethyl) dihydro-2(3H) furanone, which corresponds approximately to the esterification equilibrium, can be controlled by varying the amount of alcohol used as a solvent in the reaction.

The equilibrium can be shifted in the direction of the 3-(2'-hydroxyethyl)dihydro-2(3H)furanone by aftertreatment with small amounts of an alkali metal alkoxide in e.g. alcoholic solution. The mixture can be converted selectively into 3-(2'-acetoxyethyl)dihydro-2(3H)furanone by esterification with e.g. acetic anhydride or acetic acid, in the presence or absence of a catalyst, e.g. a strong acid such as sulfuric acid, phosphoric acid, an organic sulfonic acid such as methanesulfonic acid, benzenesulfonic acid or toluenesulfonic acid or an acidic ion exchanger.

The process according to the invention can be operated batchwise or continuously using the customary process techniques e.g. in tubular reactors or stirring vessel cascades. The catalyst, the alkali metal alkoxide, can be removed from the reaction mixture by neutralization with an acid, e.g. acetic acid, sulfuric acid or phosphoric acid, and subsequent filtering off of the precipitated salts. This facilitates further work-up according to customary processes such as distillation or extraction.

If an aqueous work-up is to be carried out, it is recommended to esterify (to acylate) the reaction mixture of 3-(2'-acetoxyethyl)dihydro-2(3H)furanone and 3-(2'-hydroxyethyl) dihydro-2(3H) furanone, since 3-(2'-acetoxyethyl)dihydro-2(3H)furanone can be extracted more easily with organic solvents.

The acetoacetic acid esters II and the alkali metal alkoxides are either known or can be easily prepared according to known processes.

The 3-(2'-oxyethyl)dihydro-2(3H)furanones I have many uses, for example for perfumes, pharmaceuticals or, on account of their polyfunctionality, as precursors for polymers. They are particularly important as starting compounds for the synthesis of pesticides. For example, 3-(2'-hydroxyethyl)dihydro-2(3H) furanone and 3-(2'-acetoxyethyl)dihydro-2(3H)furanone can be converted by the processes described in EP-A-284 969 or U.S. Pat. No. 4,837,346 into tetrahydropyran-4-carboxylic acid esters, which for their part are important intermediates for the preparation of crop protection agents as are described e.g. in EP-A-142 741.

EXAMPLES

EXAMPLE 1

A mixture of 696 g (6 mol) of methyl acetoacetate, 840 ml of methanol and 108 g of a 30% strength by weight sodium methoxide solution in methanol (0.6 mol) was initially introduced into a 3.5 l pressure container, 264 g (6.0 mol) of ethylene oxide were pumped in at 60° C. with vigorous stirring in the course of 3 hours and the mixture was then additionally stirred at 60° C. for 24 hours. The reaction discharge was flushed several times with nitrogen and the catalyst was then neutralized with 42 g (0.7 mol) of acetic acid. The low-boiling fractions were distilled off up to a distillation temperature of 55° C. at 120 mbar, and 252 g (2.2 mol) of methyl acetoacetate were recovered as an intermediate-boiling fraction at a distillation temperature of up to 78° C. at 2 mbar. 714 g (7 mol) of acetic anhydride were added dropwise to the distillation residue at 110° C. in the course of 1 hour, the mixture was additionally stirred for 1 hour and excess acetic anhydride as well as the acetic acid formed were distilled off. The residue was fractionated. 23 g (0.2 mol) of 2-acetylbutyrolactone (b.p.: 120° C./13 mbar) and 304 g (1.8 mol) of 3-(2'-acetoxyethyl)dihydro-2(3H)furanone (b.p.: 135° C./3 mbar) were obtained.

EXAMPLE 2

A mixture of 696 g (6 mol) of methyl acetoacetate, 840 ml of methanol and 108 g of a 30% strength by weight sodium methoxide solution in methanol (0.6 mol) was initially introduced into a 3.5 l pressure container, 528 g (12.0 mol) of ethylene oxide were pumped in at 60° C. with vigorous stirring in the course of 3 hours and the mixture was then additionally stirred at 60° C. for 24 hours. The reaction discharge was flushed several times with nitrogen and the catalyst was then neutralized with 42 g (0.7 mol) of acetic acid. The low-boiling fractions were distilled off up to a distillation temperature of 80° C. at 200 mbar. 714 g (7 mol) of acetic anhydride were added dropwise to the distillation residue at 110° C. in the course of 1 hour, the mixture was additionally stirred for 1 hour, excess acetic anhydride and the acetic acid formed were distilled off and the crude discharge was cooled. After adding 665 g of toluene and 200 g of water, the phases were separated and the aqueous phase was extracted once with 100 ml of toluene. After removing the solvent and rectifying, 742 g (72%) of 3-(2'-acetoxyethyl)dihydro-2(3H)furanone were obtained; b.p.: 135° C./3 mbar.

EXAMPLE 3

A mixture of 696 g (6 mol) of methyl acetoacetate, 840 ml of methanol and 216 g of a 30% strength by weight sodium methoxide solution in methanol (1.2 mol) was initially introduced into a 3.5 l pressure container, 528 g (12.0 mol) of ethylene oxide were pumped in at 40° C. with vigorous stirring in the course of 1.5 hours and the mixture was additionally stirred at 50° C. for 16 hours. The work-up was carried out as in Example 2. 692 g (67%) of 3-(2'-acetoxyethyl)dihydro-2(3H)furanone were obtained.

EXAMPLE 4

A mixture of 696 g (6 mol) of methyl acetoacetate, 840 ml of methanol and 108 g of a 30% strength by weight sodium methoxide solution in methanol (0.6 mol) was initially introduced into a 3.5 l pressure container, 528 g (12 mol) of ethylene oxide were pumped in at 40° C. with vigorous stirring in the course of 3 hours and the mixture was additionally stirred at 40° C. for 60 hours. The work-up was carried out as in Example 2. 782 g (76%) of 3-(2'-acetoxyethyl)dihydro-2(3H)furanone were obtained.

We claim:

1. A process for preparing 3-(2'-oxyethyl)dihydro-2(3H) furanones of the general formula I

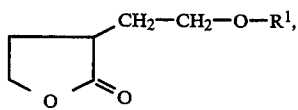

where $R^1$ is hydrogen or acetyl, by reacting ethylene oxide with acetoacetic acid esters of the general formula II

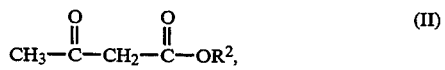

where $R^2$ is $C_1$–$C_4$-alkyl, which comprises carrying out the reaction in alcoholic solutions in the presence of alkali metal alkoxides at from 20 to 100° C. and from 1 to 20 bar.

2. A process for preparing 3-(2'-oxyethyl)dihydro-2(3H) furanones as claimed in claim 1, wherein the molar ratio of alkali metal alkoxide to acetoacetic acid ester II 0.001:1–1:1.

3. A process for preparing 3-(2'-oxyethyl)dihydro-2(3H)furanones as claimed in claim 1, wherein the molar ratio of alkali metal alkoxide to acetoacetic ester II is 0.01:1–0.5:1.

4. A process for preparing 3-(2'-oxyethyl)dihydro-2(3H) furanones as claimed in claim 1, wherein the alkali metal alkoxide is sodium or potassium $C_1$–$C_4$-alkoxide.

5. A process for preparing 3-(2'-oxyethyl)dihydro-2(3H)furanones as claimed in claim 1, wherein the alkali metal alkoxide is sodium methoxide, potassium methoxide, sodium ethoxide or potassium ethoxide.

6. A process for preparing 3-(2'-oxyethyl)dihydro-2(3H)furanones as claimed in claim 1, wherein the alkali metal alkoxide is sodium methoxide.

7. A process for preparing 3-(2'-oxyethyl)dihydro-2(3H) furanones as claimed in claim 1, wherein the alkali metal alkoxide is sodium methoxide and the alcoholic solution used is a methanolic solution.

8. A process for preparing 3-(2'-oxyethyl)dihydro-2(3H)furanones as claimed in claim 1, wherein the reaction is carried out at from 40 to 80° C.

* * * * *

UNITED STATES PATENT AND TRADEMARK OFFICE
CERTIFICATE OF CORRECTION

PATENT NO.: 5,350,863

DATED: September 27, 1994

INVENTOR(S): KUEKENHOEHNER et al.

It is certified that error appears in the above-identified patent and that said Letters Patent is hereby corrected as shown below:

IN THE CLAIMS

Column 6, claim 2, lines 13, after "II" insert -- is --.

Signed and Sealed this

Twenty-ninth Day of November, 1994

Attest:

BRUCE LEHMAN

*Attesting Officer*     *Commissioner of Patents and Trademarks*